Figure 1:
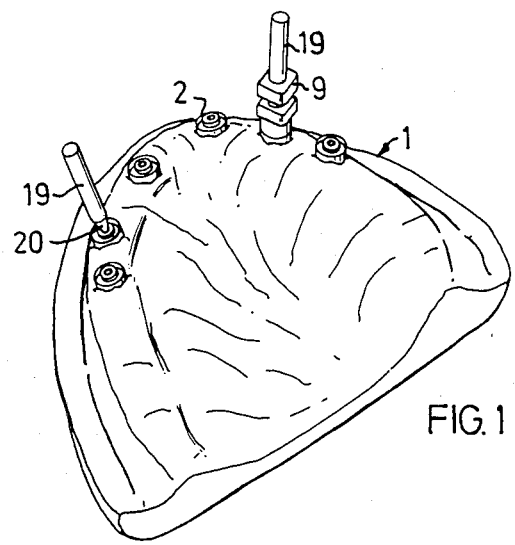

United States Patent [19]

Brånemark

[11] Patent Number: 4,708,654

[45] Date of Patent: Nov. 24, 1987

[54] POSITIVE CAST MODEL OF AN UPPER AND LOWER JAW, AND A METHOD AND MEANS FOR PRODUCING SUCH A MODEL

[75] Inventor: Per-Ingvar Brånemark, Mölndal, Sweden

[73] Assignee: The Institute for Applied Biotechnology, Gothenburg, Sweden

[21] Appl. No.: 794,827

[22] Filed: Nov. 4, 1985

[30] Foreign Application Priority Data

Nov. 20, 1984 [SE] Sweden .................. 8405825

[51] Int. Cl.⁴ ............................................. A61C 11/00
[52] U.S. Cl. ................................................ 433/213
[58] Field of Search .......................... 433/213, 214, 37

[56] References Cited

U.S. PATENT DOCUMENTS 380,021 3/1888 Carroll ..................... 433/213

Primary Examiner—Robert Peshock
Attorney, Agent, or Firm—Armstrong, Nikaido, Marmelstein & Kubovcik

[57] ABSTRACT

The present invention concerns a positive model 1 of a jaw with implanted fixture means and which is intended for the manufacture of artificial teeth attached to the fixture means via distance means 22. In the model 1 every distance organ 22 is corresponded by a dummy 2, the upper part of which having the same form as the distance organ 22, protruding over the alveolar arch, and the lower part of which including locking means for the retention of the dummy 2 in the casting material of the model 1. The invention also includes a method and means for the manufacturing of the model 1.

12 Claims, 12 Drawing Figures

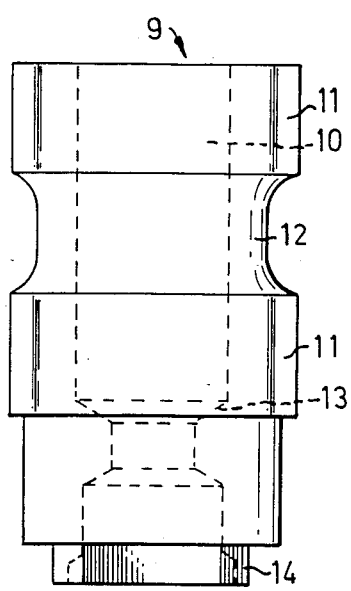
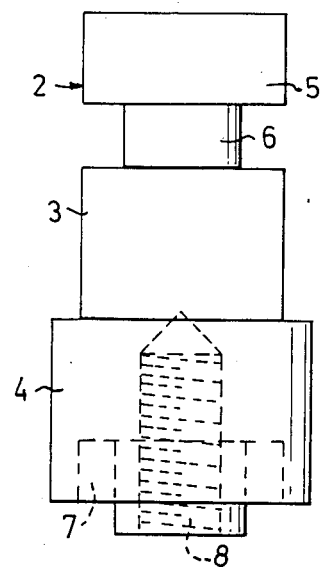
FIG.5a
FIG.6
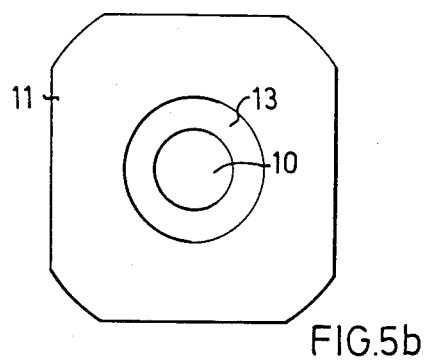
FIG.5b
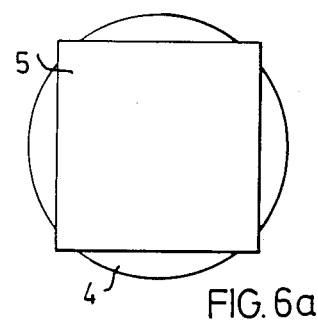
FIG.6a
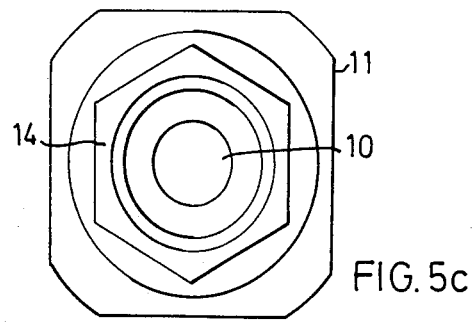
FIG.5c
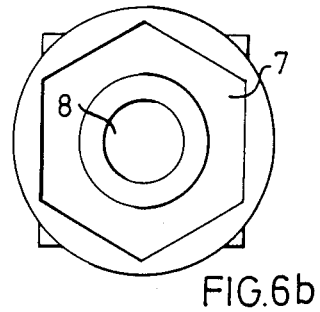
FIG.6b

POSITIVE CAST MODEL OF AN UPPER AND LOWER JAW, AND A METHOD AND MEANS FOR PRODUCING SUCH A MODEL

The present invention concerns a positive cast model of an upper or lower jaw, including one or several implanted fixture means, each of which is provided with a distance means, the upper part of which protrudes above the alveolar area and includes means for the attachment of a prosthetic appliance, the main part of the model consisting of a casting material molded in a negative impression of the upper or lower jaw.

Positive cast models of jaws are used by dental technicians for the manufacture of dentures. This way the time consuming and complicated work of fitting the denture directly into the patient can be omitted and instead the work is facilitated by working on a model of the jaw of the patient. Such models function well by the manufacture of conventional dentures as the palate is relatively smooth and does not show any steep curves or uneven projections.

However, a new method for permanent fixation of artificial teeth has been developed. In short, this method includes the implantation of a screw, preferably made from titanium, into the jawbone into a pre-drilled hole, in such a way that the upper part of the screw is level with, or situated immediately under the upper surface of the jawbone. The screw is covered by a flap of the mucous membrane and left unloaded during a rest period (3–6 months) in order to let it adhere to and form a unit with the jawbone. After the rest period the screw is uncovered and a distance means, preferably made from titanium, is attached to the screw, whereafter an artificial tooth is anchored to the distance means. By this procedure the artificial tooth must be carefully adapted to the local anatomy of the jaw. During the fitting procedure the dental technician works with a positive model of the jaw of the patient. It is made by taking a negative impression of the jaw with an impression tray, filled with impression material. The negative impression is removed from the jaw and filled with a casting material, which, after setting, represents a positive model of the jaw of the patient.

A model of a jaw with protruding distance means, however, made with this technique, has many deficiencies. For example, it is difficult by the casting procedure to obtain adequate filling for the deep holes produced by the distance means in the impression material, as air entrapments easily occur, making the cast brittle, and/or producing an inaccurate form. The greatest disadvantage, however, is that the protruding distance means which form the parts most likely to be influenced by outer forces of destruction, may chip or destruct in other ways, as conventional casting materials, for instance plaster of Paris, are relatively brittle.

Great care therefore has to be exercised when working with the working model. In spite of great caution the model may be destroyed, resulting in the need for making a new model.

The object of the present invention is to eliminate the above disadvantages and deficiencies.

This aim is achieved by the use of a model of an upper or lower jaw, described in the introduction, provided with distance means protruding over the alveolar arch, in that each distance means being in the model corresponded by a dummy, provided with an upper part having the same outer form as that of the upper part of the distance means and having the same orientation in the model as that of the distance means in the alveolar arch, and a lower part including locking means for the fixation of the dummy in the casting material.

The invention also concerns a method and means for the manufacturing of the model.

Figure 2:
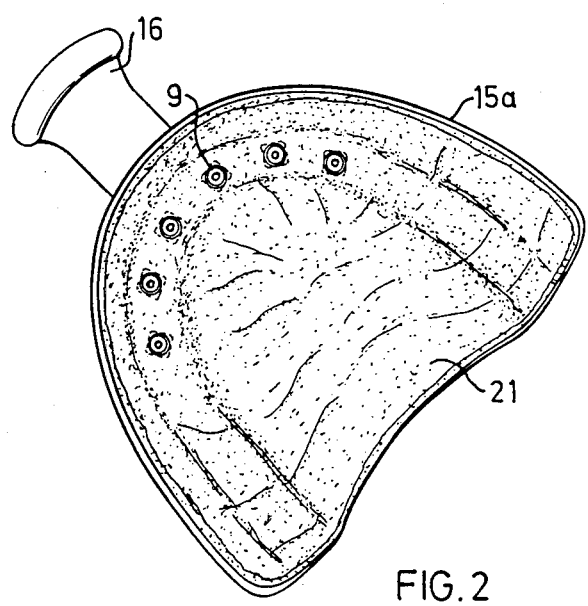
Figure 4:
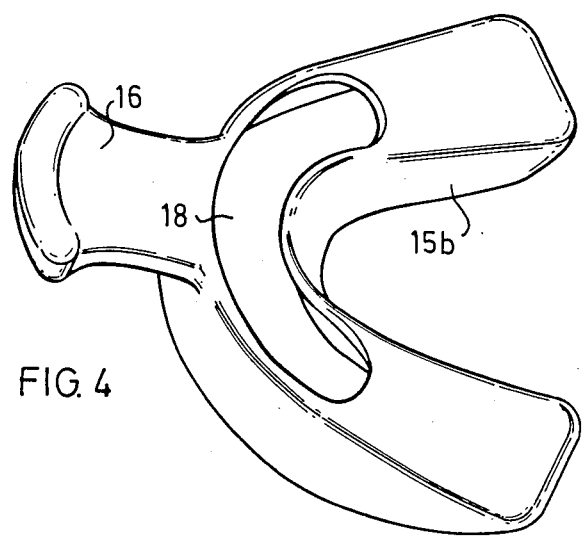
Figure 3:
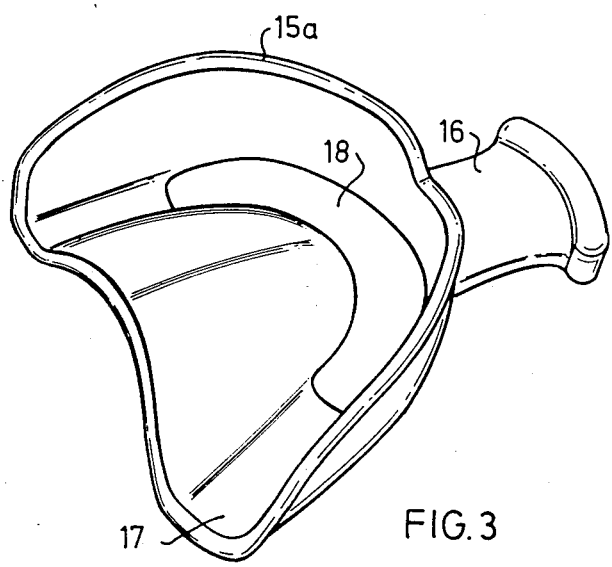
Figure 7A:
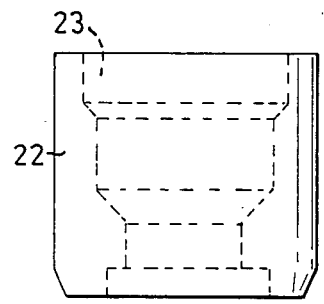
Figure 7B:
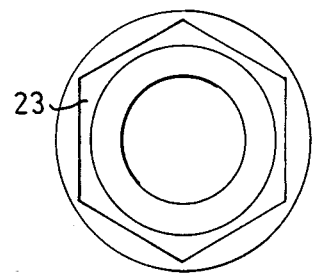

An example of the invention is described below, with reference to the attached drawings, in which:

FIG. 1 in perspective shows a model of an upper jaw, according to the invention, FIG. 2 in perspective shows an upper jaw dental tray filled with impression material, comprising a negative impression for the manufacture of the model shown in FIG. 1, FIG. 3 in perspective shows an empty upper jaw dental tray, FIG. 4 shows a lower jaw dental tray in perspective, FIG. 5a is a side view of one of the guiding elements used by the manufacture of the model shown in FIG. 1, FIG. 5b is a top plan view of the guiding element shown in FIG. 5a, FIG. 5c is a bottom plan view of the guiding element shown in FIG. 5a, FIG. 6 is a side view of a dummy used in the model shown in FIG. 1, FIG. 6a is a top plan view of the dummy shown in FIG. 6, FIG. 6b is a bottom plan view of the dummy shown in FIG. 6, FIG. 7a is a view of a distance means to be attached to a fixture means implanted into the jawbone, FIG. 7b is a top plan view of the distance means of FIG. 7a.

In FIG. 1 is shown a working model according to the invention which is used at the manufacture of a denture. The model 1 is a reproduction of an upper jaw provided with distance means 22 protruding over the alveolar ridge and attached to fixture means implanted into the jawbone. In the model 1, each distance means 22 is replaced by a dummy 2. The dummy 2 has a portion 3 to be embedded in the casting material and one portion 4 having an outer form being almost identical to that portion of the distance means, which protrudes over the alveolar arch. The portion 3 of the dummy to be embedded in the casting material comprises a square cross sectional portion 5 in order to prevent the dummy 8 from being rotated, and a circumferential groove 6 to prevent the dummy from being axially displaced in the casting material. The dummy 2 is produced from a material less sensitive to outer influences than the casting material and preferably made from metal.

The present invention also concerns a method and means for the manufacture of the model. It is of utmost importance that the dummies 2 obtain the same orientation in the final model 1 as the distance means 22 have in the jaw. In order to clarify this objective the main reference is made to FIG. 1, assuming that the figure illustrates a natural upper jaw. In the natural jaw the distance means 22 (FIG. 7a, 7b), which in the model 1 are corresponded by the dummies 2, protrude from the alveolar arch. Every distance means 22 is connected to a titanium screw implanted into the jawbone.

Before a negative impression of a jaw is taken, a guiding element 9 is attached to each distance means 22 by means of a guide pin 19. Each guiding element 9 has a through guide hole 10 for the guide pin 19. The diameter of the hole 10 is slightly larger than that of the guide pin 19. A stop means 13 is formed in the guide hole 10 cooperating with a stop member 20 provided on the guide pin 19, thereby limiting the displacement of the guide pin 19 when the guide pin 19 is screwed onto the distance means 22 or to an element attached to the distance means 22.

The guide pin 19 protrudes a considerable distance out from the guiding element 9. From the portion of the guiding element 9 which is situated closest to the distance means 22 a guide shoulder 14 protrudes, having a cross section in the form of an equilateral hexagon (see FIG. 5a and 5c). The upper portion of the distance means is provided with a corresponding hexagonal depression 23 (FIG. 7a, 7b). The guiding element 9 is guided and prevented from rotating by the engagement of the shoulder 14 into the depression 23 when the guiding element 9 is attached to the distance means 22.

When all distance means 22 have been provided with guide elements 9 and axially protruding guide pins 19, a dental impression tray 15a, 15b filled with softened impression material 21 is applied over the jaw. The impression tray 15a, 15b has a conventional design, including a handle 16 and a through-like depression 17, see FIG. 3 and 4, showing a tray 15a for the upper jaw and a tray 15b for the lower jaw, respectively. The impression tray differs however from conventional impression trays by the fact that an opening 18 is provided in the through-like depression 17 over the alveolar ridge. This way the guide pins 19 will protrude from the back side of the impression tray 15a, 15b when the tray is applied to a jaw. After the solidifying of the impression material the guide pins are released from the respective distance means 22, which can be accomplished by means of the portion of the guide pins 19, which protrudes out from the backside of the impression tray 15a, 15b. The tray is then removed from the mouth, whereby the guiding elements 9 are retained in the solidified impression material. In order to improve the adherence of the guiding elements 9 to the impression material 21 (see FIG. 5a) they are provided with a peripheral groove 12 which prevents the guide elements 9 from being axially displaced in the impression material, and a portion 11 with an almost square cross section, preventing rotation in the impression material.

A dummy 2 is then attached on each guide element 9 by means of the guide pin 19. The dummy 2 (FIG. 6a, 6b, 6c) has the same outer form as the distance means 22 at the end situated closest to the guide element 9, and is supplied with a corresponding hexagonal depression 7, into which the shoulder 14 of the guide element 9 engages, as well as a threaded hole 8 for the guide pin 19.

The negative impression, retaining the guiding elements 9, the guide pins 19 and the dummies 2, is then filled with a casting material that is left to solidify, whereafter the guide pins 19 are released from the dummies 2 so that the impression tray with the attached guiding elements 9 can be removed from the finished positive model 1 with the dummies 2 remaining fixed in the solidified casting material.

I claim:

1. Positive cast model of a lower or upper jaw, including one or several fixture means implanted into the jawbone, each of which is provided with a distance means, having an upper portion protruding over the alveolar arch and means for the attachment of a prosthetic appliance, the main part of the model consisting of a casting material molded in a negative impression of the lower or upper jaw, characterized in that each distance means is in the model replaced by a dummy made of a harder matrial than the casting material, provided with an upper portion having the same outer form as that of the upper portion of the distance means and having the same orientation in the model as that of the distance means in the alveolar arch, and a lower portion having locking means for the fixation or the dummy in the casting material.

2. A model according to claim 1, characterized in that the locking means of the dummy comprises a portion having a non-circular cross section.

3. A model according to claim 2, characterized in that the non-circular portion of the dummy has an essentially square cross section.

4. A model according to claim 2, characterized in that the locking means of the dummy has means for axial locking of the dummy in the casting material.

5. A model according to claim 4, characterized in that the axial locking means of the dummy has a partly or completely circumferential groove.

6. A model according to claims 1-5, characterized in that the dummy comprises a guide means cooperating with complementary guide means of a guiding element.

7. A model according to claim 6, characterized in that the guide means of the dummy includes a depression receiving a shoulder protruding from the guiding element.

8. A model according to claim 7, characterized in that the depression has a non-circular cross section.

9. A model according to claim 8, characterized in that the cross section of the depression has the form of an equilateral hexagon.

10. A method for the manufacture of a positive model of a lower or upper jaw, including one or several fixture means implated into the jawbone, each of which is provided with a distance means protruding over the alveolar arch, the upper portion of the distance means including means for the attachment of an artificial tooth or prothesis, characterized by the following steps:

attaching a guiding element onto each distance means by means of a fastening means, fitting a dental tray filled with softened impression material upon the jaw provided with guiding elements and leaving the impression material to solidify, releasing the guiding element from the distance means while maintaining the guiding element in unchanged positions in the solidified impression material, taking out the dental tray from the mouth with the guiding elements embedded in the impression material, attaching a dummy made of a harder material than the casting material onto each guiding element, the dummy and situated closest to the guiding element having the same contour as that of the above the alveolar arch protruding portion of the distance means, filling the negative impression, provided with dummies, with the casting material and leaving it to solidfy, releasing each guiding element from its corresponding dummy, and finally, removing the impression material with remaining guiding elements from the completed solidifed positive model.

11. A method according to claim 10, characterized in that each guiding element comprises a through guide hole and stop means, and in that each fastening means is an elongated guide pin provided with a threaded end and a sidewisely protruding stop means, the guide pin being passed through and guided in the guide hole and screwed into the distance means or into an element connected to the distance means or into the dummy, while the stop means of the guide pin being arranged to engage with the stop means of the guiding element.

12. A method according to claim 11, characterized in that the impression tray is designed with an opening above the guide pins whereby these have such a length that they protrude through the opening of the impression tray and protrude over the back side of the impression tray when the tray is applied over the jaw during the impression procedure.

* * * * *